(12) United States Patent
Gui et al.

(10) Patent No.: US 11,105,767 B1
(45) Date of Patent: Aug. 31, 2021

(54) METHOD FOR PREPARING DUAL-FUNCTIONAL HYBRID THIN-FILM FOR SELF-CALIBRATION DETECTION OF TUMOR-DERIVED EXOSOMES

(71) Applicant: QINGDAO UNIVERSITY, Qingdao (CN)

(72) Inventors: Rijun Gui, Qingdao (CN); Yujiao Sun, Qingdao (CN); Hui Jin, Qingdao (CN)

(73) Assignee: QINGDAO UNIVERSITY, Qingdao (CN)

( * ) Notice: Subject to any disclaimer, the term of this patent is extended or adjusted under 35 U.S.C. 154(b) by 0 days.

(21) Appl. No.: 17/051,782

(22) PCT Filed: Nov. 8, 2019

(86) PCT No.: PCT/CN2019/116519
§ 371 (c)(1),
(2) Date: Oct. 30, 2020

(87) PCT Pub. No.: WO2021/087945
PCT Pub. Date: May 14, 2021

(30) Foreign Application Priority Data

Nov. 7, 2019 (CN) .......................... 201911078972.1

(51) Int. Cl.
*G01N 27/327* (2006.01)
*G01N 33/574* (2006.01)
(Continued)

(52) U.S. Cl.
CPC ........... *G01N 27/3278* (2013.01); *B05D 1/00* (2013.01); *B82Y 30/00* (2013.01); *C07H 21/00* (2013.01);
(Continued)

(58) Field of Classification Search
None
See application file for complete search history.

(56) References Cited

U.S. PATENT DOCUMENTS

2017/0137870 A1   5/2017   Krishnan et al.

FOREIGN PATENT DOCUMENTS

CN   108872564 A   11/2018
CN   109133014 A   1/2019
(Continued)

OTHER PUBLICATIONS

W.J. Shen, et al., "Cu-based Metal—Organic Frameworks as a Catalyst To Constructs Ratiometric Electrochemical Aptasensor for Sensitive Lipopolysaccharide Detection", Analytical Chemistry, 87(22): p. 11345-11352, Nov. 2015.*
(Continued)

*Primary Examiner* — J. Christopher Ball
(74) *Attorney, Agent, or Firm* — Bayramoglu Law Offices LLC

(57) ABSTRACT

A method for preparing a dual-functional hybrid thin-film for self-calibration detection of tumor-derived exosomes is disclosed. A dual-functional hybrid thin-film, aptamer-BPNSs/Fc/ZIF-67/ITO, is constructed by facile self-assembly of a cobalt-based metal-organic framework (ZIF-67) composite doped with black phosphorus nanosheets (BPNSs), an aptamer and ferrocene (Fc) on an indium tin oxide (ITO) electrode. Methylene blue (MB) labeled aptamer specifically binds to CD63 protein to precisely capture protein. The protein is a specific biomolecule carried by breast cancer MCF-7 cell exosome, and realizes the detection of the tumor cell exosome. A self-calibration sensor for quantitative detection of the tumor exosome is constructed by using MB as a response signal and Fc as a reference. Compared with the prior art, the present invention features convenient operation, high sensitivity, low cost and excellent specificity, and can be used as a novel exosome self-calibration detection method for quantitative detection of the exosomes in biomedical samples.

1 Claim, 2 Drawing Sheets

(51) Int. Cl.
    *G01N 27/416*     (2006.01)
    *B05D 1/00*     (2006.01)
    *B82Y 30/00*     (2011.01)
    *C12N 15/115*     (2010.01)
    *C09K 11/58*     (2006.01)
    *C07H 21/00*     (2006.01)

(52) U.S. Cl.
    CPC ............ *C09K 11/58* (2013.01); *C12N 15/115* (2013.01); *G01N 27/3277* (2013.01); *G01N 27/4163* (2013.01); *G01N 33/57415* (2013.01); *G01N 33/57484* (2013.01); *G01N 33/57488* (2013.01); *C12N 2310/16* (2013.01); *G01N 2333/70596* (2013.01)

(56) References Cited

FOREIGN PATENT DOCUMENTS

| | | |
|---|---|---|
| CN | 109239040 A | 1/2019 |
| CN | 109307700 A | 2/2019 |
| CN | 109529064 A | 3/2019 |
| CN | 109655512 A | 4/2019 |
| CN | 109813786 A | 5/2019 |
| CN | 110108881 A | 8/2019 |
| WO | 2017087914 A2 | 5/2017 |
| WO | 2017090050 A1 | 6/2017 |

OTHER PUBLICATIONS

Ali Ahmadi et al., A rapid and simple ratiometric fluorescent sensor for patulin detection based on a stabilized DNA duplex probe containing less amount of aptamerinvolved base pairs, Taianta, 2019,pp. 641-646, 204.

Hong Li et al., Recent developments in dopamine-based materials for cancer diagnosis and therapy, Advances in Colloid and Interface Science, 2018, pp. 1-20, 252.

Ling Zhu et al., Label-Free Quantitative Detection of Tumor-Derived Exosomes through Surface Plasmon Resonance Imaging, Analytical Chemistry, 2014, pp. 8857-8864, 86.

Yaokun Xia et al., A visible and colorimetric aptasensor based on DNA-capped single-walled carbon nanotubes for detection of exosomes, Biosensors and Bioelectronics, 2017, pp. 8-15, 92.

\* cited by examiner

METHOD FOR PREPARING DUAL-FUNCTIONAL HYBRID THIN-FILM FOR SELF-CALIBRATION DETECTION OF TUMOR-DERIVED EXOSOMES

CROSS REFERENCE TO THE RELATED APPLICATIONS

This application is the national phase entry of International Application No. PCT/CN2019/116519, filed on Nov. 8, 2019, which is based upon and claims priority to Chinese Patent Application No. 201911078972.1, filed on Nov. 7, 2019, the entire contents of which are incorporated herein by reference.

TECHNICAL FIELD

The present invention relates to the technical field of preparation of functionalized hybrid thin-film materials and tumor exosome sensors, and more particularly, relates to a preparation method of a self-assembled dual-functional hybrid thin-film material based on a cobalt-based metal-organic framework composite doped with black phosphorus nanosheets (BPNSs) and ferrocene (Fc). The thin-film material prepared by the method can be used for precise capture of CD63 transmembrane protein and self-calibration detection of breast cancer exosomes.

BACKGROUND

Exosomes are extracellular vesicles with a size of ranging between 50-100 nm. They are released from multivesicular bodies via intracellular lysosomal pathways. Exosomes carry a large number of macromolecules from parental cells, including transmembrane and cytoplasmic proteins, mRNA, DNA, and micro-RNA. Exosomes serve as messengers for mediating intercellular information and play an important role in detecting diseases, especially cancer-related conditions. Use of exosomes as biomarkers has shown promise recently in early cancer detection and diagnosis. The use of exosomes has helped to alleviate problems like cost prohibition and low sensitivity that are characteristic of previously dominant invasive cancer screening and detection processes.

The scientific literature is replete with reports relating to the quantitative detection of exosomes. Existing detection technology, however, remains challenging in application, and it is difficult to achieve direct and specific analysis of nanoscale exosomes. For example, flow cytometry (FCM) detection is limited by weak light scattering, while nanoparticle tracking analysis (NTA) lacks specificity. In the early stages of the disease, exosomal concentration is low, and new and improved methods are needed to achieve super-sensitive detection of exosomes. Current methods for exosomal detection include FCM, NTA, surface plasmon resonance (SPR), colorimetry, luminescence, and electrochemical analysis. For example, Zhu et al. used SPR imaging technology to achieve quantitative detection of exosomes (Ling Zhu, Kun Wang, Jian Cui, Huan Liu, Xiangli Bu, Huailei Ma, Weizhi Wang, He Gong, Christopher Lausted, Leroy Hood, Guang Yang, Zhiyuan Hu, Label-free quantitative detection of tumor-derived exosomes through surface plasmon resonance imaging, 2014, *Analytical Chemistry*, 86, 8857-8864). Xia et al. constructed a colorimetric detection method of exosomes based on DNA-capped single-walled carbon nanotubes (Yaokun Xia, Mengmeng Liu, Liangliang Wang, An Yan, Wenhui He, Mei Chen, Jianming Lan, Jiaoxing Xu, Lunhui Guan, Jinghua Chen, A visible and colorimetric aptasensor based on DNA-capped single-walled carbon nanotubes for detection of exosomes, 2017, *Biosensors and Bioelectronics*, 92, 8-15). L I Zhiyang et al. used G-quadruplex-Hemin to simulate a $H_2O_2$ reaction catalyzed by peroxidase to generate signals, combined with rolling circle amplification to synthesize a large number of G-quadruplexes for signal amplification to achieve quantitative detection of exosomes (L I Zhiyang, H E Nongyue and HUANG Rongrong, Chinese National Invention Patent Publication No. CN109655512A, titled Method for detecting exosome based on aptamer and rolling circle amplification). WANG Guosheng developed a product integrating of isolation and purification of exosomes with specific semi-quantitative detection of exosomes, and constructed an exosome-based in vitro real-time detection platform (WANG Guosheng, Exosome-based in vitro real-time detection platform and detection method thereof, Chinese National Invention Patent Publication No. CN108872564A).

Although works relating to quantitative detection of exosomes have been published internationally, achieving direct and specific, super-sensitive detection of nanoexosomes efficiently and at a low cost remains elusive. Based on this need, the present invention provides a method for preparing a BPNSs/Fc/ZIF-67 dual-functional hybrid thin-film material based on a cobalt-based metal-organic framework (ZIF-67) composite doped with black phosphorus nanosheets (BPNSs) and ferrocene (Fc), which is easily self-assembled on an indium tin oxide (ITO) film electrode. The thin-film material can be used for precise capture of CD63 transmembrane protein and self-calibration detection of breast cancer MCF-7 cell-secreted exosomes. As of the filing date of this patent application, Chinese and overseas literature and patent publications germane to the preparation of the BPNSs/Fc/ZIF-67 dual-functional hybrid thin-film material, and the use of the thin-film material applied in the self-calibration detection of tumor-derived exosomes have not been uncovered.

SUMMARY

The objective of the present invention is to overcome the problems existing in the prior art mentioned above and design a method for detecting tumor-derived exosomes with convenient operation, high sensitivity, low cost and excellent specificity.

To achieve the above-mentioned objective, the present invention provides a dual-functional hybrid thin-film for self-calibration detection of tumor-derived exosomes, and a preparation method of the hybrid thin-film includes the following steps:

(1) preparation of a Fc/ZIF-67 composite: weighing a predetermined amount of $Co(NO_3)_2 \cdot 6H_2O$ and 2-methylimidazole into a mixed solvent containing 47 mL of ethanol and 3 mL of deionized water, magnetically stirring to form an uniform mixed solution, and adjusting concentrations of $Co(NO_3)_2 \cdot 6H_2O$ and 2-methylimidazole to 0.1-0.5 mol/L and 0.8-1.5 mol/L, respectively; adding the mixed solution to an electrolytic cell; with Ag/AgCl as a reference electrode, platinum wire as a counter electrode, and indium tin oxide (ITO) as a working electrode, electrodepositing an Fc/ZIF-67 composite on the surface of the ITO electrode through cyclic voltammetry at a constant voltage of −5 to −10 V for 100-500 s;

(2) preparation of a BPNSs/Fc/ZIF-67 composite: weighing 10-30 mg of black phosphorus crystals and adding into 50 mL of 1-methyl-2-pyrrolidone; after sonicating in an ultrasonic cleaner for 1-6 h, transferring to a probe-type ultrasonic generator and sonicating for 1-4 h; centrifuging a product dispersion for 15 min at 12,000 rpm, and centrifuging an upper dispersion for 15 min at 5,000 rpm; adding a prepared BPNSs dispersion dropwise to a surface of the Fc/ZIF-67 composite, drying naturally, to obtain the BPNSs/Fc/ZIF-67 composite on the surface of the ITO electrode;

(3) preparation of an aptamer-BPNSs/Fc/ZIF-67 hybrid thin-film: immersing a BPNSs/Fc/ZIF-67/ITO film electrode in phosphate buffered saline (PBS) containing 1-10 µM of CD63 transmembrane protein corresponding to single-stranded DNA aptamer, incubating at 37° C. for 30-120 min, taking out the film electrode, drying naturally, to obtain an aptamer-BPNSs/Fc/ZIF-67 composite on the surface of the ITO electrode, i.e., the aptamer-BPNSs/Fc/ZIF-67 hybrid thin-film; and (4) preparation of a hybrid thin-film sensor: placing a hybrid thin-film as a working electrode in a three-electrode system of an electrochemical workstation, adding exosomes extracted from breast cancer MCF-7 cells in the PBS as an electrolyte, and measuring electrochemical square wave voltammetry curves at different concentrations of the exosomes; with methylene blue (MB) modified on an aptamer strand as a response signal, Fc doped in the ZIF-67 metal-organic framework as a reference signal, and ratios of peak current intensities $I_{Fc}/I_{MB}$ as self-calibrated signal output, fitting a linear relationship between ratios of $I_{Fc}/I_{MB}$ and concentrations of the exosomes to construct a self-calibrating sensor for quantitative detection of the exosomes, in which a linear detection range of concentrations of the tumor-derived exosomes is $1\times10^2$–$1\times10^6$ particles $\mu L^{-1}$, and a detection limit is 50-100 particles $\mu L^{-1}$.

The advantages of the present invention are as follows: The present invention provides a dual-functional hybrid thin-film material based on a ZIF-67 composite doped with BPNSs, an aptamer and Fc, which is facilely self-assembled on an ITO film electrode, i.e., aptamer-BPNSs/Fc/ZIF-67/ITO. Methylene blue (MB)-labeled single-stranded DNA aptamer specifically binds to CD63 transmembrane protein to achieve precise capture of CD63 transmembrane protein. CD63 transmembrane protein is a specific macromolecule carried by breast cancer MCF-7 cell-secreted exosomes and can be used as a biomarker to detect breast cancer MCF-7 cell-secreted exosomes. Using MB as a response signal, ferrocene (Fc) doped in ZIF-67 as a reference signal, and the ratios of peak current intensities $I_{Fc}/I_{MB}$ as self-calibrated signal output, a linear relationship between $I_{Fc}/I_{MB}$ and concentrations of the exosomes is fitted to construct a self-calibrating sensor for quantitative detection of tumor-derived exosomes. Compared with the prior art, the method of the present invention features convenient operation, high sensitivity, low cost, and excellent specificity, can be used as a novel self-calibration detection method of the exosomes, and is used for quantitative detection of the exosomes in biomedical samples.

DETAILED DESCRIPTION OF THE EMBODIMENTS

The present invention will be described in detail below with reference to the drawings.

Embodiment 1

Figure 1:
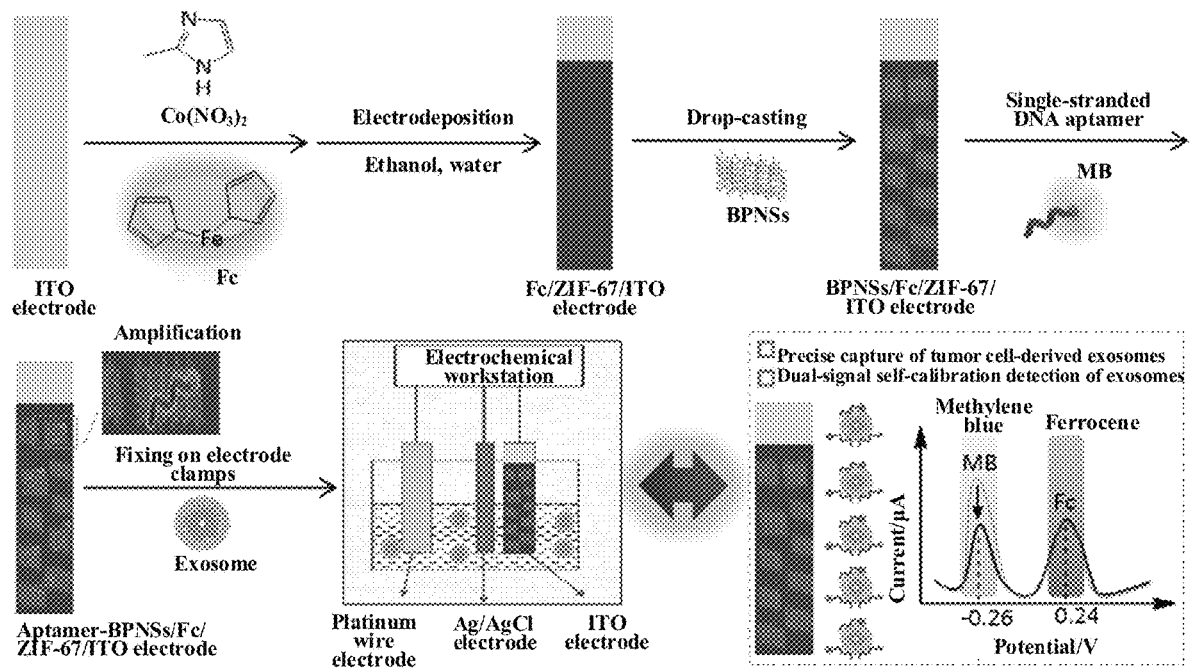
FIG. 1 is a schematic diagram showing a preparation of a self-assembled dual-functional hybrid thin-film material based on a cobalt-based metal-organic framework composite doped with BPNSs and Fc, and a principle of application thereof in precise capture of CD63 transmembrane protein and self-calibration detection of breast cancer exosomes.

A schematic diagram of the preparation method and detection principle of a self-assembled dual-functional hybrid thin-film based on a cobalt-based metal-organic framework composite doped with BPNSs and Fc according to embodiment 1 is shown in FIG. 1, and the specific preparation steps are as follows:

Preparation of a Fc/ZIF-67 composite: A predetermined amount of $Co(NO_3)_2 \cdot 6H_2O$ and 2-methylimidazole were weighed in a mixed solvent containing 47 mL of ethanol and 3 mL of deionized water, and magnetically stirred to form an uniform mixed solution. Concentrations of $Co(NO_3)_2 \cdot 6H_2O$ and 2-methylimidazole were adjusted to 0.1 and 0.8 mol/L, respectively. The mixed solution was added to an electrolytic cell; with Ag/AgCl as a reference electrode, platinum wire as a counter electrode, and ITO as a working electrode. An Fc/ZIF-67 composite was electrodeposited on the surface of the ITO electrode through cyclic voltammetry at a constant voltage of −5 V for 100 s.

Preparation of a BPNSs/Fc/ZIF-67 composite: 10 mg of black phosphorus crystals were weighed and added into 50 mL of 1-methyl-2-pyrrolidone, sonicated in an ultrasonic cleaner for 1 h, and then transferred to a probe-type ultrasonic generator and sonicated for 1 h. A product dispersion was centrifuged for 15 min at 12,000 rpm, and an upper dispersion was centrifuged for 15 min at 5,000 rpm. A prepared BPNSs dispersion was added dropwise to the surface of the Fc/ZIF-67 composite, followed by natural drying, and the BPNSs/Fc/ZIF-67 composite was prepared on the surface of the ITO electrode.

Preparation of an aptamer-BPNSs/Fc/ZIF-67 hybrid thin-film: A BPNSs/Fc/ZIF-67/ITO film electrode was immersed in phosphate buffered saline (PBS) containing 1 µM of CD63 transmembrane protein corresponding to single-stranded DNA aptamer, and incubated at 37° C. for 30 min. The film electrode was taken out and dried naturally, and an aptamer-BPNSs/Fc/ZIF-67 composite was prepared on the surface of the ITO electrode, i.e., the aptamer-BPNSs/Fc/ZIF-67 hybrid thin-film was prepared.

Figure 2A:
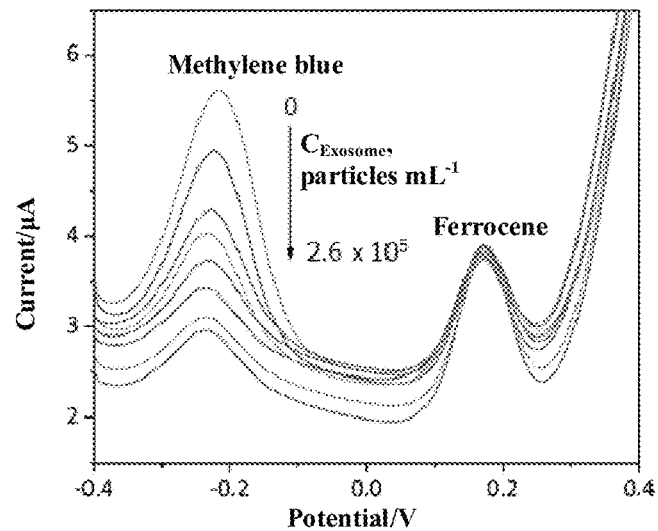
FIG. 2A is a diagram showing electrochemical square wave voltammetry curves determined with the hybrid thin-film material as a working electrode at different concentrations of the exosomes.
Figure 2B:
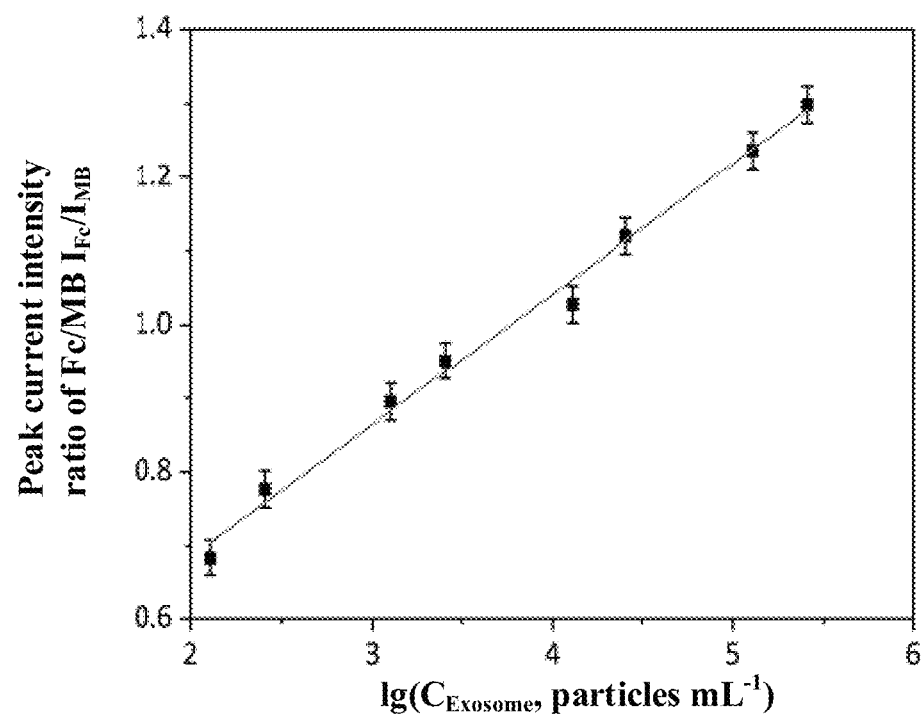
FIG. 2B is a diagram showing a linear relationship between different ratios of $I_{Fc}/I_{MB}$ and concentrations of the exosomes fitted by ratios of redox peak current intensities $I_{Fc}/I_{MB}$ of ferrocene versus methylene blue corresponding to different concentrations of the exosomes.

Preparation of a hybrid thin-film sensor: A hybrid thin-film as a working electrode was placed in a three-electrode system of an electrochemical workstation, exosomes extracted from breast cancer MCF-7 cells were added in PBS as an electrolyte, and electrochemical square wave voltammetry curves were measured at different concentrations of the exosomes (as shown in FIG. 2A). With MB modified on an aptamer strand as a response signal, Fc doped in the ZIF-67 metal-organic framework as a reference signal, and ratios of peak current intensities $I_{Fc}/I_{MB}$ as self-calibrated signal output, a linear relationship between $I_{Fc}/I_{MB}$ ratio and concentrations of the exosomes (as shown in FIG. 2B) was fitted to construct a self-calibrating sensor for quantitative detection of the exosomes. A linear detection range of concentrations of the tumor-derived exosomes was $1.3 \times 10^2 - 2.6 \times 10^5$ particles $\mu L^{-1}$, and a detection limit was 60 particles $\mu L^{-1}$.

Embodiment 2

A self-assembled dual-functional hybrid thin-film based on a cobalt-based metal-organic framework composite doped with BPNSs and Fc according to the embodiment had the same preparation method and detection principle as embodiment 1, and other specific preparation steps are as follows:

Preparation of a Fc/ZIF-67 composite: A predetermined amount of $Co(NO_3)_2 \cdot 6H_2O$ and 2-methylimidazole were weighed in a mixed solvent containing 47 mL of ethanol and 3 mL of deionized water, and magnetically stirred to form an uniform mixed solution. Concentrations of $Co(NO_3)_2 \cdot 6H_2O$ and 2-methylimidazole were adjusted to 0.3 and 1.2 mol/L, respectively. The mixed solution was added to an electrolytic cell; with Ag/AgCl as a reference electrode, platinum wire as a counter electrode, and ITO as a working electrode, an Fc/ZIF-67 composite was electrodeposited on the surface of the ITO electrode through cyclic voltammetry at a constant voltage of −8 V for 200 s.

Preparation of a BPNSs/Fc/ZIF-67 composite: 20 mg of black phosphorus crystals were weighed and added into 50 mL of 1-methyl-2-pyrrolidone, sonicated in an ultrasonic cleaner for 3 h, and then transferred to a probe-type ultrasonic generator and sonicated for 2 h. A product dispersion was centrifuged for 15 min at 12,000 rpm, and an upper dispersion was centrifuged for 15 min at 5,000 rpm. A prepared BPNSs dispersion was added dropwise to the surface of the Fc/ZIF-67 composite, followed by natural drying, and the BPNSs/Fc/ZIF-67 composite was prepared on the surface of the ITO electrode.

Preparation of an aptamer-BPNSs/Fc/ZIF-67 hybrid thin-film: A BPNSs/Fc/ZIF-67/ITO film electrode was immersed in PBS containing 4 $\mu M$ of CD63 transmembrane protein corresponding to single-stranded DNA aptamer, and incubated at 37° C. for 50 min; the film electrode was taken out and dried naturally, and an aptamer-BPNSs/Fc/ZIF-67 composite was prepared on the surface of the ITO electrode, i.e., the aptamer-BPNSs/Fc/ZIF-67 hybrid thin-film was prepared.

Preparation of a hybrid thin-film sensor: A hybrid thin-film as a working electrode was placed in a three-electrode system of an electrochemical workstation, exosomes extracted from breast cancer MCF-7 cells were added in PBS as an electrolyte, and electrochemical square wave voltammetry curves were measured at different concentrations of the exosomes. With MB modified on an aptamer strand as a response signal, Fc doped in the ZIF-67 metal-organic framework as a reference signal, and ratios of peak current intensities $I_{Fc}/I_{MB}$ as self-calibrated signal output, a linear relationship between $I_{Fc}/I_{MB}$ ratio and concentrations of the exosomes was fitted to construct a self-calibrating sensor for quantitative detection of the exosomes. A linear detection range of concentrations of the tumor-derived exosomes was $1.0 \times 10^2 - 1.0 \times 10^5$ particles $\mu L^{-1}$, and a detection limit was 50 particles $\mu L^{-1}$.

Embodiment 3

A self-assembled dual-functional hybrid thin-film based on a cobalt-based metal-organic framework composite doped with BPNSs and Fc according to the embodiment had the same preparation method and detection principle as embodiment 1, and other specific preparation steps are as follows:

Preparation of a Fc/ZIF-67 composite: A predetermined amount of $Co(NO_3)_2 \cdot 6H_2O$ and 2-methylimidazole were weighed in a mixed solvent containing 47 mL of ethanol and 3 mL of deionized water, and magnetically stirred to form an uniform mixed solution. Concentrations of $Co(NO_3)_2 \cdot 6H_2O$ and 2-methylimidazole were adjusted to 0.5 and 1.5 mol/L, respectively. The mixed solution was added to an electrolytic cell; with Ag/AgCl as a reference electrode, platinum wire as a counter electrode, and ITO as a working electrode, an Fc/ZIF-67 composite was electrodeposited on the surface of the ITO electrode through cyclic voltammetry at a constant voltage of −10 V for 400 s.

Preparation of a BPNSs/Fc/ZIF-67 composite: 30 mg of black phosphorus crystals were weighed and added into 50 mL of 1-methyl-2-pyrrolidone, sonicated in an ultrasonic cleaner for 5 h, and then transferred to a probe-type ultrasonic generator and sonicated for 4 h. A product dispersion was centrifuged for 15 min at 12,000 rpm, and an upper dispersion was centrifuged for 15 min at 5,000 rpm. A prepared BPNSs dispersion was added dropwise to the surface of the Fc/ZIF-67 composite, followed by natural drying, and the BPNSs/Fc/ZIF-67 composite was prepared on the surface of the ITO electrode.

Preparation of an aptamer-BPNSs/Fc/ZIF-67 hybrid thin-film: A BPNSs/Fc/ZIF-67/ITO film electrode was immersed in PBS containing 8 $\mu M$ of CD63 transmembrane protein corresponding to single-stranded DNA aptamer, and incubated at 37° C. for 100 min. The film electrode was taken out and dried naturally, and an aptamer-BPNSs/Fc/ZIF-67 composite was prepared on the surface of the ITO electrode, i.e., the aptamer-BPNSs/Fc/ZIF-67 hybrid thin-film was prepared.

Preparation of a hybrid thin-film sensor: A hybrid thin-film as a working electrode was placed in a three-electrode system of an electrochemical workstation, exosomes extracted from breast cancer MCF-7 cells were added in PBS as an electrolyte, and electrochemical square wave voltammetry curves were measured at different concentrations of the exosomes. With MB modified on an aptamer strand as a response signal, Fc doped in the ZIF-67 metal-organic framework as a reference signal, and ratios of peak current intensities $I_{Fc}/I_{MB}$ as self-calibrated signal output, a linear relationship between $I_{Fc}/I_{MB}$ ratio and concentrations of the exosomes was fitted to construct a self-calibrating sensor for quantitative detection of the exosomes. A linear detection range of concentrations of the tumor-derived exosomes was $1.0 \times 10^3 - 1.0 \times 10^6$ particles $\mu L^{-1}$, and a detection limit was 80 particles $0^{-1}$.

The foregoing descriptions are merely preferred embodiments of the present invention. It should be noted that several variations and modifications can be made by those skilled in the art without departing from the principles of the present invention and should also fall within the protection scope of the invention.

What is claimed is:

1. A method for preparing a dual-functional hybrid thin-film for a self-calibration detection of tumor-derived exosomes, comprising:
   (1) preparation of a ferrocene-doped cobalt-based metal-organic framework (Fc/ZIF-67) composite: weighing a predetermined amount of $Co(NO_3)_2 \cdot 6H_2O$ and 2-methylimidazole and adding the predetermined amount of $Co(NO_3)_2 \cdot 6H_2O$ and 2-methylimidazole into a mixed solvent containing 47 mL of ethanol and 3 mL of deionized water to obtain a first mixture, magnetically stirring the first mixture to form an uniform first mixture, and adjusting a concentration of the Co(NO$_3$)$_2$·6H$_2$O to 0.1-0.5 mol/L and adjusting a concentration of the 2-methylimidazole to 0.8-1.5 mol/L, respectively; adding the uniform first mixture to an electrolytic cell; with Ag/AgCl as a reference electrode, platinum wire as a counter electrode, and indium tin oxide (ITO) as a first working electrode, electrodepositing the Fc/ZIF-67 composite on a surface of the first working electrode through a cyclic voltammetry at a constant voltage of −5 to −10 V for 100 to 500 s;

(2) preparation of a black phosphorus nanosheets and ferrocene-doped cobalt-based metal-organic framework (BPNSs/Fc/ZIF-67) composite: weighing 10-30 mg of black phosphorus crystals and adding the black phosphorus crystals into 50 mL of 1-methyl-2-pyrrolidone to obtain a second mixture; sonicating the second mixture in an ultrasonic cleaner for 1-6 h, transferring the second mixture to a probe-type ultrasonic generator and sonicating the second mixture for 1-4 h to obtain a product dispersion; centrifuging the product dispersion for 15 min at 12,000 rpm to obtain an upper dispersion, and centrifuging the upper dispersion for 15 min at 5,000 rpm to obtain a black phosphorus nanosheets (BPNSs) dispersion; adding the black phosphorus nanosheets (BPNSs) dispersion dropwise to a surface of the Fc/ZIF-67 composite to obtain a third mixture, drying the third mixture naturally, to obtain the BPNSs/Fc/ZIF-67 composite on the surface of the first working electrode as a BPNSs/Fc/ZIF-67/ITO film electrode;

(3) preparation of an aptamer-BPNSs/Fc/ZIF-67 hybrid thin-film: immersing the BPNSs/Fc/ZIF-67/ITO film electrode in phosphate buffered saline (PBS) containing 1-10 μM of CD63 transmembrane protein corresponding to a single-stranded DNA aptamer to obtain a fourth mixture, incubating the fourth mixture at 37° C. for 30-120 min to obtain a resulting film electrode, taking out the resulting film electrode, drying the resulting film electrode naturally, to obtain an aptamer-BPNSs/Fc/ZIF-67 composite on the surface of the first working electrode, wherein the aptamer-BPNSs/Fc/ZIF-67 composite on the surface of the first working electrode is the aptamer-BPNSs/Fc/ZIF-67 hybrid thin-film; and (4) preparation of a hybrid thin-film sensor: placing the aptamer-BPNSs/Fc/ZIF-67 hybrid thin-film in a three-electrode system of an electrochemical workstation, wherein the aptamer-BPNSs/Fc/ZIF-67 hybrid thin-film serves as a second working electrode, adding exosomes in PBS, wherein the exosomes are extracted from breast cancer MCF-7 cells and the PBS serves as an electrolyte, and measuring electrochemical square wave voltammetry curves at different concentrations of the exosomes; with methylene blue (MB) modified on an aptamer strand as a response signal, Fc doped in the ZIF-67 metal-organic framework as a reference signal, and ratios of peak current intensities $I_{Fc}/I_{MB}$ as a self-calibrated signal output, fitting a linear relationship between the ratios of the $I_{Fc}/I_{MB}$ and the concentrations of the exosomes to construct a self-calibrating sensor for a quantitative detection of the exosomes, wherein a linear detection range of the concentrations of the exosomes is $1\times10^2$-$1\times10^6$ particles $\mu L^{-1}$, and a detection limit is 50-100 particles $\mu L^{-1}$.

* * * * *